US008226661B2

(12) United States Patent
Balling et al.

(10) Patent No.: US 8,226,661 B2
(45) Date of Patent: Jul. 24, 2012

(54) DEVICE AND METHOD FOR MANIPULATING AND INSERTING ELECTRODE ARRAYS INTO NEURAL TISSUES

(75) Inventors: Kyle Balling, Salt Lake City, UT (US); Garett Robertson, North Salt Lake, UT (US); Lael Stander, Provo, UT (US); Richard A. Normann, Park City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1156 days.

(21) Appl. No.: 12/055,053

(22) Filed: Mar. 25, 2008

(65) Prior Publication Data
US 2008/0221589 A1    Sep. 11, 2008

Related U.S. Application Data

(63) Continuation-in-part of application No. 11/970,375, filed on Jan. 7, 2008, now abandoned.

(60) Provisional application No. 60/878,781, filed on Jan. 5, 2007.

(51) Int. Cl.
*A61B 19/00* (2006.01)
(52) U.S. Cl. ........................................ 606/129
(58) Field of Classification Search ........................ None
See application file for complete search history.

(56) References Cited

U.S. PATENT DOCUMENTS

| 5,361,760 | A  | * | 11/1994 | Normann et al. ............ 600/377 |
| 6,149,657 | A  |   | 11/2000 | Kuzma |
| 6,304,785 | B1 |   | 10/2001 | McCreery et al. |
| 6,968,238 | B1 |   | 11/2005 | Kuzma |
| 7,018,384 | B2 |   | 3/2006  | Skakoon |
| 7,033,326 | B1 |   | 4/2006  | Pianca et al. |
| 7,063,708 | B2 |   | 6/2006  | Gibson et al. |
| 8,024,022 | B2 | * | 9/2011  | Schulman et al. ............ 600/372 |

OTHER PUBLICATIONS

Bai et al "A high yield microassembly structure for three dimensional microelectrode arrays" IEEE, vol. 47 No. 3 Mar. 2000 p. 281-289.*
Agnew et al "Safe and effective stimulation of neural tissue" quarterly progress report Oct. 1-Dec. 31, 1998.*
Rousche, et al.; a Method for Pneumatically Inserting an Array of Penetrating Electrodes into Cortical Tissue; Annals of Biomedical Engineering, vol. 20; pp. 413-422; 1992.

* cited by examiner

*Primary Examiner* — Gary Jackson
*Assistant Examiner* — Amy Shipley
(74) *Attorney, Agent, or Firm* — Thorpe North & Western LLP (57) ABSTRACT

An insertion device for inserting a therapeutic device into organic tissue is disclosed and described. The device is particularly suited to insertion of such as nerve stimulating electrode arrays. The insertion device has at least one controllable positive pressure source (greater than atomospheric), two vacuum sources and a dual vacuum pressure control system. The positive pressure and the dual vacuum pressure control systems are manipulated to allow the manipulation and insertion or retrieval of a therapeutic device. The insertion device can be spatially manipulated by hand, without requiring other equipment for positioning the insertion device.

18 Claims, 7 Drawing Sheets

DEVICE AND METHOD FOR MANIPULATING AND INSERTING ELECTRODE ARRAYS INTO NEURAL TISSUES

RELATED APPLICATION

This application is a continuation-in-part of U.S. patent application Ser. No. 11/970,375, filed Jan. 7, 2008 which claims the benefit of U.S. Provisional Application No. 60/878,781, filed Jan. 5, 2007, which are each incorporated herein by reference.

FIELD OF THE INVENTION

The present invention is directed toward a therapeutic device insertion device that can be spatially manipulated by hand, and can insert a therapeutic device into organic tissues by utilizing a pneumatic, high-speed insertion mechanism.

BACKGROUND OF THE INVENTION AND RELATED ART

Therapeutic devices can be used for a wide variety of reasons. As an example, a therapeutic device like the Utah Electrode Array (UEA) or the Utah Slanted Electrode Array (USEA) may be inserted into nerve tissue to allow the array to receive electrical signals from or deliver electrical signals to the nerve tissue. Such an array can be implanted in any type of nerve tissue. The UEA is described in U.S. Pat. No. 5,361,760, which is hereby fully incorporated by this reference.

Many different types of therapeutic device insertion devices have been developed for inserting a therapeutic device. Previous insertion devices have two main limitations: they do not allow the insertion device to be spatially manipulated by hand, and the insertion devices are unable to retrieve the therapeutic device from the organic tissue. The insertion speed of previous insertion devices is relatively slow, for example 1-4 meters per second. This relatively slow insertion speed made it probable that complete electrode array insertion might not occur during insertion. Also, conventional techniques required the time consuming use of mechanical, robotic or other equipment to reliably position the electrode array prior to insertion.

SUMMARY OF THE INVENTION

In light of the problems and deficiencies inherent in the prior art, the present invention seeks to overcome these by using an insertion technique that greatly increases the insertion speed for the insertion device and minimizes the time required for array positioning. The insertion device can also retrieve the therapeutic device after it has been inserted.

In accordance with the invention as embodied and broadly described herein, the present invention includes the use of two vacuum sources as a primary means of inserting a therapeutic device. Control of the two vacuum provides effective control of placement of a therapeutic device using a vacuum tip. Further, the present invention allows the insertion device to be spatially manipulated by hand, as opposed to requiring other equipment to position the insertion device prior to insertion. The insertion speed of the present invention can generally be approximately 8-12 meters per second although other speeds can be achieved and may be suitable in some circumstances. For example, an additional compression source can be fluidly associated with the vacuum tip to allow for application of a positive pressure sufficient to accelerate the therapeutic device towards neural tissue.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

DETAILED DESCRIPTION OF EXEMPLARY EMBODIMENTS

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

Definitions

In describing and claiming the present invention, the following terminology will be used.

The singular forms "a," "an," and "the" include plural referents unless the context clearly dictates otherwise. Thus, for example, reference to "a vacuum" includes reference to one or more of such devices and reference to "inserting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context. As used herein with respect to two parts or elements, "connected" refers to any appropriate means for connecting the two elements, such as complimentary threads, adhesives or other mechanical connections. For example, and not by way of limitation, one element may include inside threads corresponding to outside threads on another element. Similarly, one element may have a diameter that is substantially identical to the diameter of another element and these two elements could be connected by abutting the two elements and cementing them together with an appropriate adhesive.

As used herein, "fluid communication" refers to a continuous unimpeded fluid path between two volumes, such that fluids, e.g. gases, can flow between the two volumes substantially unimpeded.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

In the present disclosure, the term "preferably" or "preferred" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Embodiments of the Invention

The present invention describes a method and system for inserting therapeutic devices into organic tissue such as nerve or brain tissue. The present invention provides several significant advantages over prior related insertion devices, some of which are recited here and throughout the following more detailed description. First, the manipulation of multiple pressure sources, e.g. two vacuum sources and a positive pressure source, allows for improved handling of a therapeutic device, while also allowing high insertion speeds. The use of vacuum to secure the electrode array to the tip of the inserter allows the present insertion device to be spatially manipulated by hand without requiring the aid of other equipment. Also, the use of vacuum delivered to the tip of the inserter can be used to attach and retrieve a therapeutic device from organic tissue by adjusting relative vacuum sources as described in more detail below.

Each of the above-recited advantages will be apparent in light of the detailed description set forth below, with reference to the accompanying drawings. These advantages are not meant to be limiting in any way. Indeed, one skilled in the art will appreciate that other advantages may be realized, other than those specifically recited herein, upon practicing the present invention.

Figure 1:
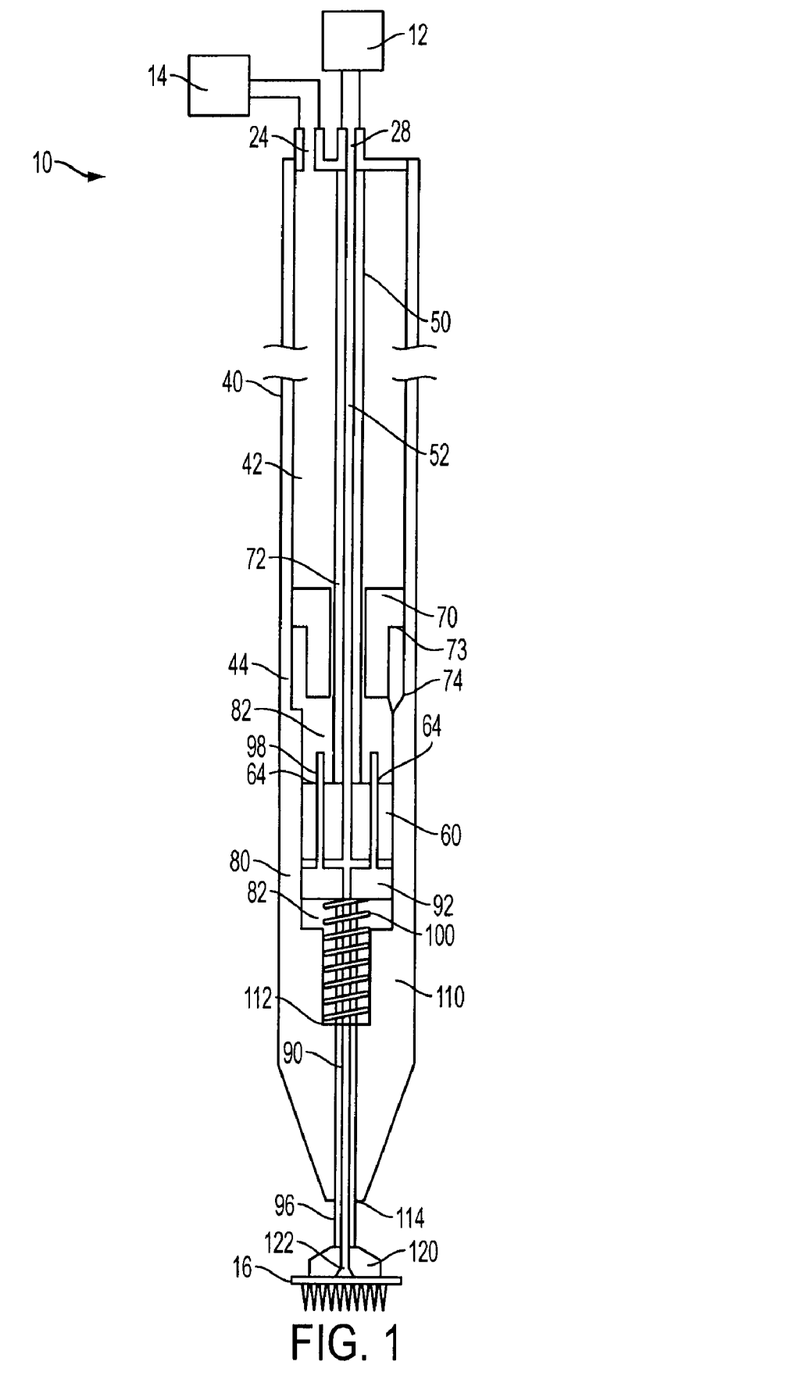
FIG. 1 is a side cross-sectional view of the insertion device having a UEA retained at the tip in accordance with one embodiment of the present invention.

Although illustrated in FIGS. 1-12 generally, two primary embodiments are described in connection with FIGS. 1-10 and 11-12, respectively. FIG. 1 in particular shows one insertion device 10 of the present insertion. The insertion device may be composed of a number of parts or elements and the configuration and assembly of each of the parts may vary depending on the particular embodiment of the insertion device, or the therapeutic device 16 intended to be inserted. Generally, the insertion device 10 may comprise an optional adaptor 20 (shown in FIG. 2), two vacuum sources (12 and 14), a outside barrel 40, a central tube 50, a piston 70, a piston stop 60, a housing 80, an inserter 90, a position bias member 100, a head 110, and a tip 120. These individual parts or elements can generally be formed of metals, polymers, alloys, composites and/or other suitable materials. Typically, they can be formed of stainless steel, although other materials such as titanium, ceramic, or high-density polyurethane can also be suitable. For example, polymers may be suitable for single use or low use embodiments, while titanium, stainless steel and the like can be more suitable for devices intended for repeated use over months or years. The position bias member can generally be a spring, although other mechanisms can also be used such as, but not limited to, flexible tabs, elastic restraints, and the like.

Figure 11:
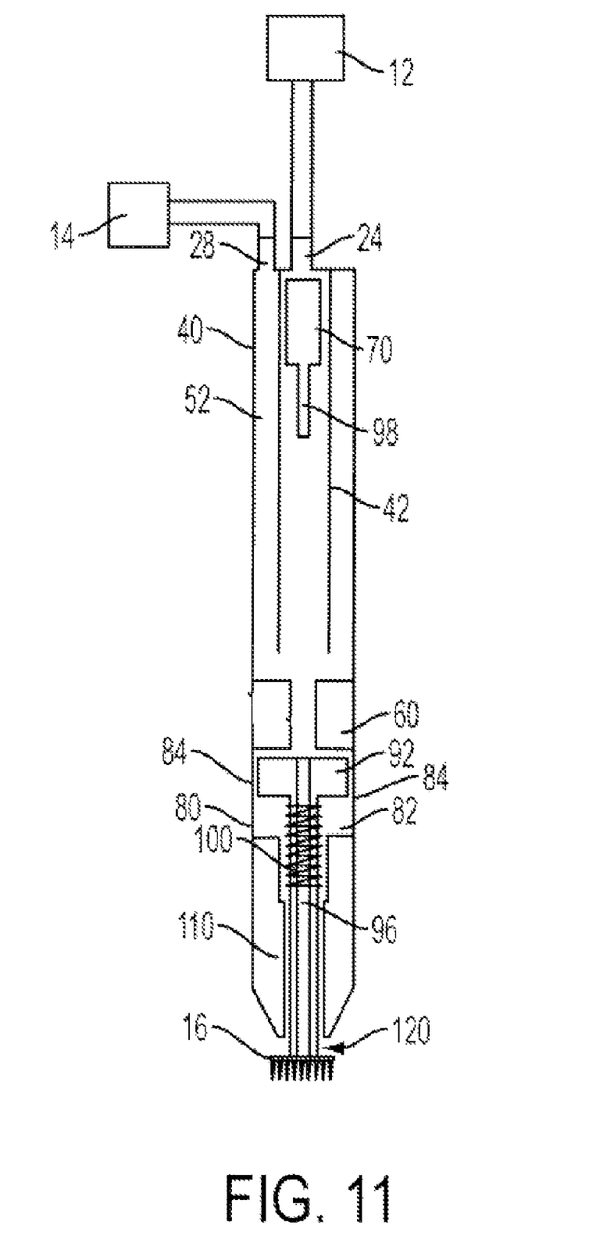
FIG. 11 is a side cross-sectional view of the insertion device in accordance with another embodiment of the present invention.

Referring again to FIG. 1, the insertion device 10 can include the piston 70 which is slidably oriented in an inner chamber 42 such that the piston can slide along the inner chamber from one end to an opposite end. The piston 70 may be restricted to movement within the outside barrel 40 between the upper proximal end of the outside barrel 40 and the piston stop 60 at the distal end of the outside barrel 40. The piston stop 60 can be oriented at one end and can be associated with an inserter which is located opposite the piston across the piston stop. A momentum transfer member can be oriented on either or both of the piston and the inserter. In FIG. 1 the momentum transfer member 98 is oriented on the inserter via members which extend through apertures in the piston stop. Alternatively, the momentum transfer member 98 can be analogously oriented on the piston 70 as shown in FIG. 11. The inserter can include the momentum transfer member, a shaft 96, and tip 120 as separate removable pieces (as shown in FIG. 1) or as a single integrated piece. A vacuum line can be associated with the inserter to allow for selective application of suction at the tip. Typically, a vacuum source can be pulled through vacuum line 28 which is in fluid communication with the tip in order to retain a desired therapeutic device thereon.

Another piston vacuum source and a positive pressure source connected via inlet line 24 can be used to drive the piston up or down the outer barrel 40. Alternatively, movement of the piston can be driven using a combination of the two vacuum sources and a positive pressure source applied to a back and front side of the piston, respectively. This alternative is described in more detail below in connection with FIG. 11.

Figure 2:
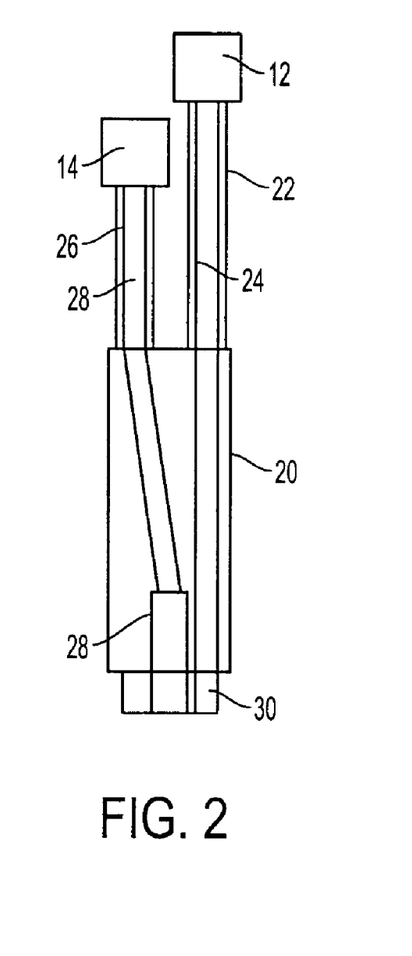
FIG. 2 is a side cross-sectional view of a vacuum connection adapter of the insertion device in accordance with one embodiment of the present invention.

As shown in FIG. 2, an adaptor 20 facilitates the connection of the two vacuum sources 12 and 14 to the insertion device 10. The adaptor 20 can be generally cylindrical in shape with two connectors extending from the top of the adaptor, a first vacuum connector 22 and a second vacuum connector 26. Each of these connectors may be cylindrical in shape and can be operatively connected to each of the vacuum sources.

The first vacuum connector 22 defines a first vacuum conduit 24 and may be operatively attached to the first vacuum 12. Similarly, the second vacuum connector 26 defines a second vacuum conduit 28 and may be operatively attached to the second vacuum 14 and a positive pressure (not shown). The adaptor 20 may also be configured to allow attachment to the outside barrel 40 (shown in FIGS. 1 and 5), at an outside barrel connection 30 where the vacuum conduits 24 and 28 line up with vacuum inlet lines 24 and 28 shown in FIG. 1. The connection can be interference fit, recessed slots, threaded, or any other suitable attachment mechanism.

In one embodiment of the insertion device, the first pressure conduit 24 may be substantially linear through the adaptor 20 and adjacent the perimeter of the adaptor 20 and the second vacuum conduit 28 may begin adjacent the perimeter of the adaptor 20 and angle through the adaptor 20 to a central position of the adaptor 20 as illustrated in FIG. 2. The second vacuum conduit 28 may increase in diameter at the distal end of the adaptor 20 near the outside barrel connection 30 to allow for insertion or connection with the proximal end of a central tube 50. The connection between the second vacuum conduit 28 and the central tube 50 may be accomplished by any appropriate means and can be designed for connection to various diameter vacuum tubing or the like. Typically, the vacuum tubing can be connected to the inlet conduits via interference fitting although compression fittings, threaded fittings, or other suitable fittings can be used.

Figure 3:
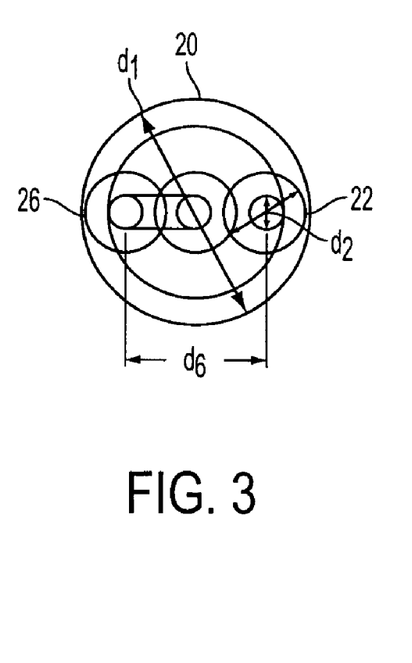
FIG. 3 is a plan bottom view of the adapter of FIG. 2.
Figure 4:
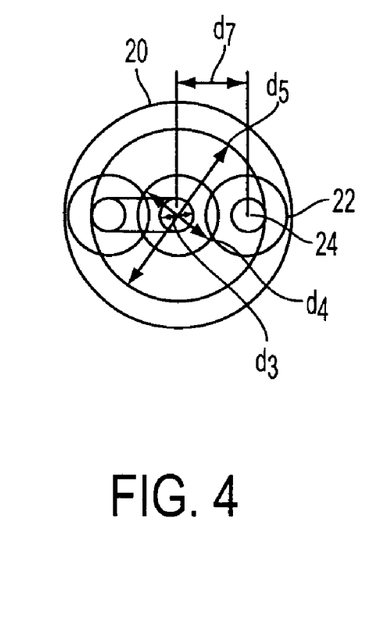
FIG. 4 is a plan top view of the adapter of FIG. 2.
Figure 6:
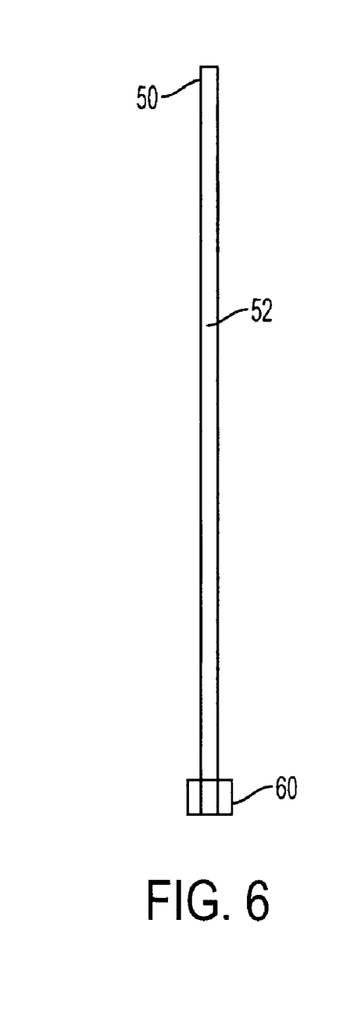
FIG. 6 is a perspective view of the central tube connected to the piston stop of the insertion device in accordance with one embodiment of the present invention.

In one very specific embodiment shown in FIGS. 3 and 4, the adaptor 20 can be 1.0 inches in length and have a diameter ($d_1$) of 0.375 inches. The first vacuum connector 22 can be 0.75 inches in length and the first vacuum conduit 24 can have a diameter ($d_2$) of 0.0626 inches. The second vacuum connector 26 can be 0.5 inches in length and the second vacuum conduit 28 can have a diameter ($d_3$) of 0.0626 inches. Moreover, the distal end of the second vacuum conduit 28 can have an increased diameter ($d_4$) of 0.125 inches and have inside threads to facilitate attachment to the central tube 50, which central tube 50 is shown in FIG. 6. The outside barrel connection 30 on the adaptor 20 can have a diameter ($d_5$) of 0.30 inches. In this manner the distance between the vacuum lines can be reduced from a first distance ($d_6$) of 0.2294 inches to a second distance ($d_7$) of 0.115 inches as shown in FIGS. 3 and 4, respectively.

Figure 5:
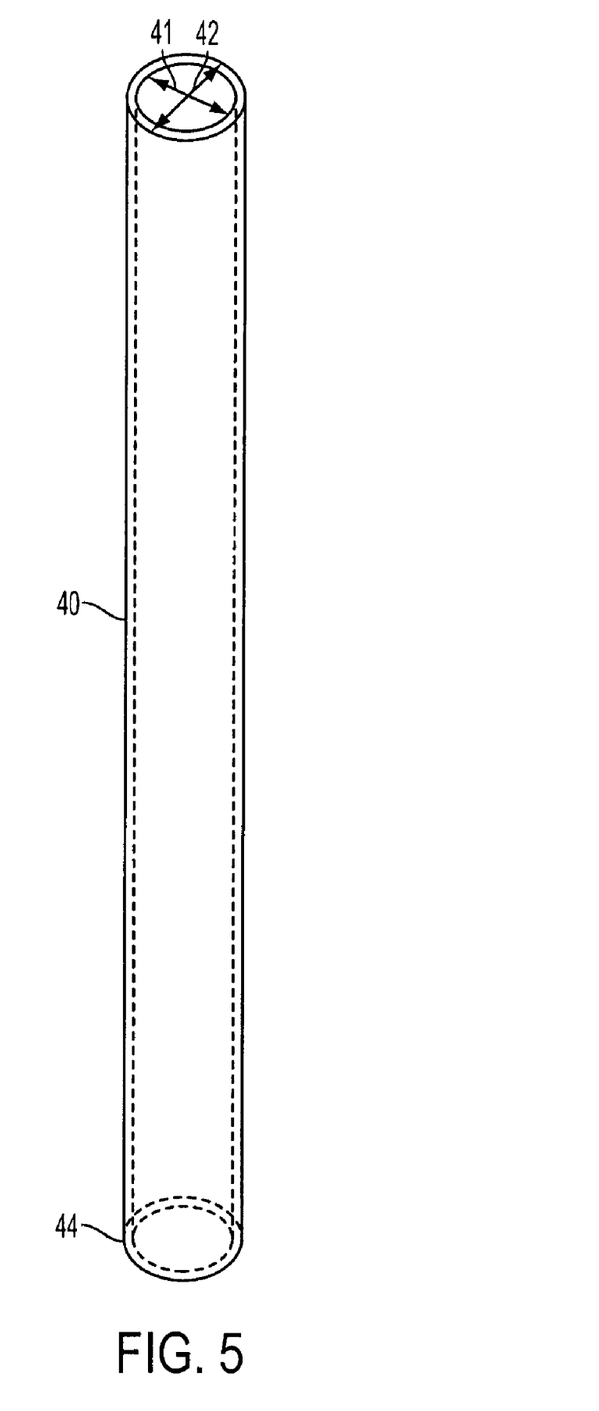
FIG. 5 is a perspective view of the outside barrel of the insertion device in accordance with one embodiment of the present invention.

The adaptor 20, shown in FIGS. 2-4, may be connected at the outside barrel connection 30 to a proximal end, or first end, of the outside barrel 41, shown in FIG. 5, by any appropriate means. As shown in FIG. 5, the outside barrel 40 is generally cylindrical and defines an inner chamber 42. The outside barrel 40 may be of varying dimensions depending upon the size of the therapeutic device 16 to be inserted. In one embodiment, the outside barrel size can be configured to ergonomically facilitate hand-held operation of the device. As such, the diameter for such embodiments can range from about 0.2 to about 0.5 inches and in one case 0.3750 inches (with an inside diameter of about 0.3016 inches), although other sizes can also be suitable. Similarly, the overall length of the device can typically be from about 3 to about 9 inches such as about 6.0 inches, although other dimensions can be used as long as the insertion speed and accuracy are maintained. Referring again to FIG. 1, the inner chamber 42 is in fluid communication with the first vacuum conduit 24. The outside barrel 40 may also contain the central tube 50 and slidably contain the piston 70. The outside barrel 40 may include a housing connection 44 (also shown in FIG. 5) at a distal end, or second end, of the outside barrel 40.

As mentioned previously, the central tube 50 may be connected to the second vacuum conduit 28 and positioned along a central, transverse axis inside the outside barrel 40. The central tube 50 defines an axial chamber 52. The axial chamber is in fluid communication with the second vacuum conduit 28. The central tube 50 may have a piston stop 60 connected to a distal end of the central tube 50 as either an integral piece as shown in FIGS. 1 and 6-8, or as a separate annular sleeve. In this embodiment, the inner chamber 42 is concentrically oriented around at least a portion of the axial chamber (i.e. above the piston stop 60 such that the inner chamber has an annular volume). Further, the axial chamber and the inner chamber are fluidly independent from one another such that the first vacuum controls the piston movement while the second vacuum extends through the axial chamber to the tip of the device sufficient to retain a microelectrode array thereon. In this embodiment, each of the axial chamber and the inner chamber are fluidly independent and can be substantially isolated from the other.

Figure 7:
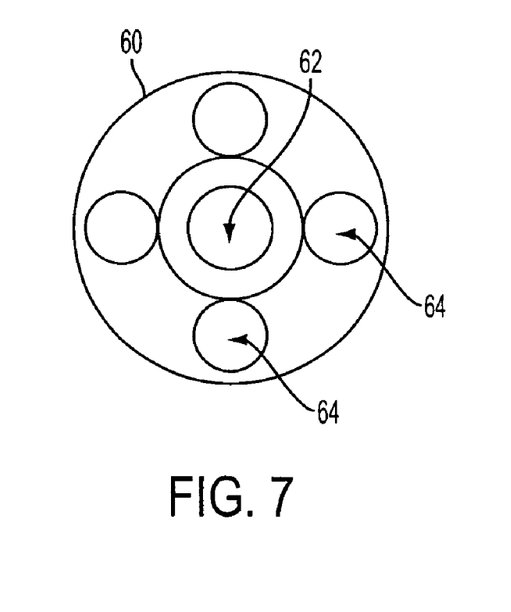
FIG. 7 is a bottom plan view of the piston stop of FIG. 6.
Figure 8:
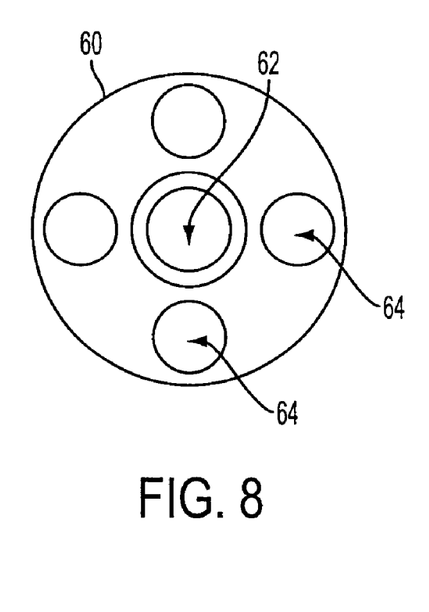
FIG. 8 is a top plan view of the piston stop of FIG. 6.

The piston stop 60 enables the transfer of momentum and/or mechanical energy from the piston 70 to the inserter 90 via the momentum transfer member 98. The piston stop is also configured to limit the motion of the piston 70. The piston stop 60 may generally be described as a disc, cylinder or block having at least one aperture. Referring now to FIGS. 7 and 8, the piston stop has a central stop aperture 62 and at least one radial stop aperture 64. The central stop aperture 62 allows fluid communication between the axial chamber 52 and a tip 120 via an inserter conduit 96 (shown in FIG. 1). In this way, the central tube 50 may be connected to the piston stop 60 at the central stop aperture 62. As shown in FIG. 1, the radial stop apertures 64 allow momentum transfer members 98 associated with the inserter 90 to extend through the piston stop 60.

Dimensions of the piston stop can vary. For example, and not by way of limitation, FIG. 7 shows a piston stop 60 having a diameter of 0.3126 inches and a height of 0.25 inches. The central stop aperture 62 of this embodiment can have a diameter of 0.069 inches, while the radial stop apertures 64 may have a diameter of 0.08 inches. These dimensions can vary, for example, based on the momentum transfer member design.

Referring now to FIG. 1, the piston 70 provides the momentum and/or mechanical energy to actuate the inserter 90 upon impact with the momentum transfer member 98. The piston 70 can have a weight and size designed for insertion with a particular therapeutic device and/or insertion speed. Further, several pistons of varying weights can be provided with a single insertion device 10, which are readily interchangeable. Using pistons of different masses would be helpful when the therapeutic device being inserted is of a respectively different mass. A change in therapeutic device mass would be directly proportional to a change in piston mass to conserve the same momentum transfer from the piston to the therapeutic device. For example, inserting a UEA with a wireless transmitter chip on the back increases mass and would be appropriate to use a piston of greater mass. In one embodiment of the present invention, the piston 70 includes a piston aperture 72 that allows the piston 70 to be slidably engaged along the outside of the central tube 50. The piston can include an optional lip 73 which prevents movement of the piston past a corresponding step 74 in the housing 80. Thus, the piston can be sized and designed such that the piston is halted by contact with either the step 74, the piston stop 60, or both simultaneously, as long as the momentum transfer members 98 are sufficiently contacted to trigger the inserter. The width of the step can vary but in one case can be about 0.06 inches.

The piston dimensions can vary, for example and not by way of limitation, the piston 70 can have a total length of 0.5 inches, the proximal length, or upper length, of the piston 70 can be 0.125 inches in length and can have a diameter of 0.3 inches. The distal length, or lower length, of the piston 70 can be 0.375 inches in length and have a diameter of 0.25 inches while the piston aperture 72 can have a diameter of 0.125 inches.

The housing 80 provides the structural support for the transfer of momentum and/or mechanical energy in the insertion device 10. The housing 80 may be generally cylindrical and defines the inserter chamber 82. The housing section encloses the piston stop and other members where high impact occurs. Therefore, the housing section can generally be made of robust material exhibiting sufficient strength to withstand repeated impacts over the expected useful life of the device. The housing may be connected to the distal end, or second end, of the outside barrel 40 at the proximal end, or first end, of the housing 80. The housing also provides a head connection 86 and may be connected to the head 110 thereby. The inserter chamber can be substantially isolated from the inner chamber 42 as well as the axial chamber 52 and also enclosed so as to be isolated from external atmosphere. The distal end of the housing 80, or head connection 86, can have inside threads to facilitate connection with the head 110 or can be connected via interference fitting or other suitable approach.

Figure 9:
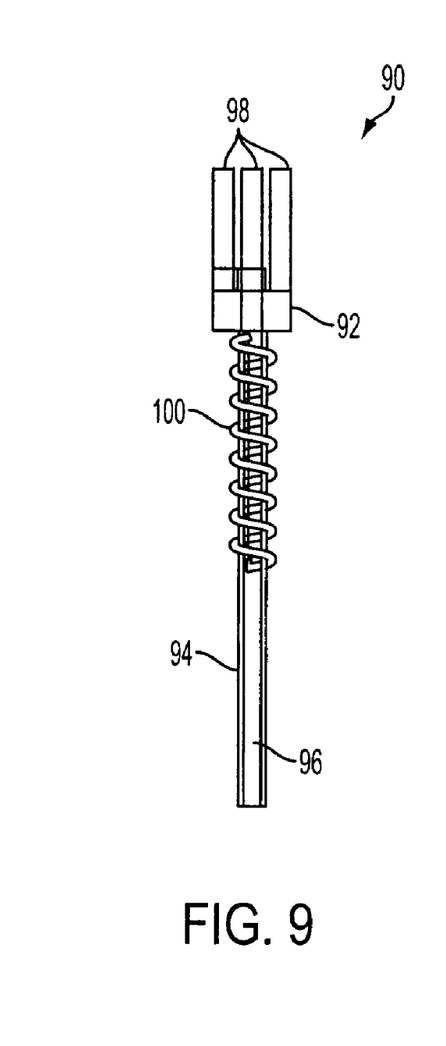
FIG. 9 is a side view of the momentum transfer member of the insertion device in accordance with one embodiment of the present invention.
Figure 10:
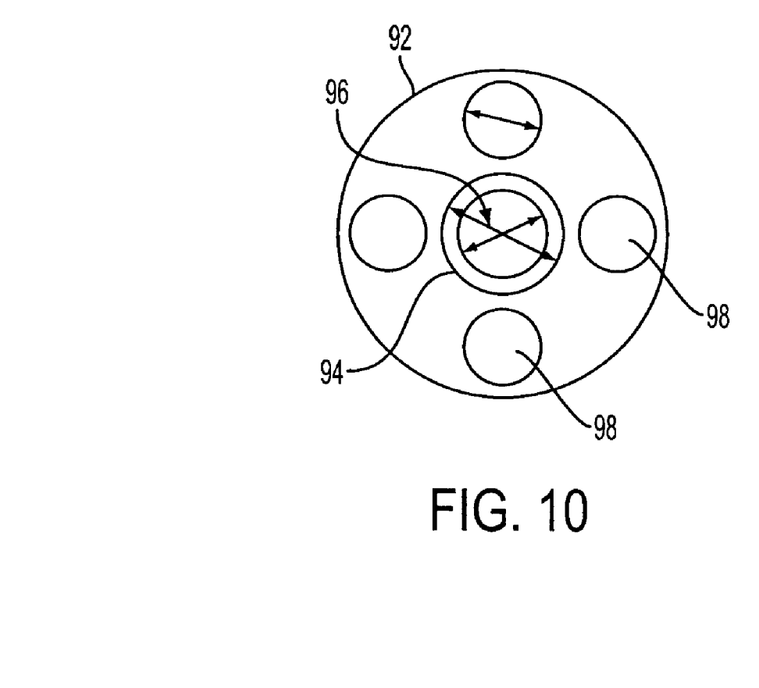
FIG. 10 is a top plan view of the momentum transfer member of FIG. 9.

Referring now to FIG. 9, the inserter 90 provides the structure for retaining and inserting the therapeutic device. The inserter may be configured to have an inserter head 92 at the proximal end, or first end, of an inserter shaft 94. The inserter shaft defines an inserter conduit 96 along a transverse axis of the inserter shaft. The inserter conduit is in fluid communication with the axial chamber via an aperture extending through the inserter head (more readily seen on FIG. 10). As shown in FIG. 1, the inserter head 92 is positioned adjacent the distal side of the piston stop 60. The inserter head 92 is kept adjacent the distal side of the piston stop 60 by a position bias member 100 (e.g. a spring) in a biased position. Referring again to FIG. 9, the inserter 90 can have at least one momentum transfer member 98 attached to the inserter head 92. FIG. 10 shows a configuration of four momentum transfer members 98 oriented radially about the center aperture opening of the inserter conduit 96. Referring back to FIG. 1, the momentum transfer member 98 may be sized and positioned to extend through a corresponding radial stop aperture 64. In this manner, the inserter 90 may be actuated by the piston 70 by momentum transfer and/or mechanical means as it impacts the momentum transfer members.

Although the dimensions can vary, FIG. 10 illustrates an inserter head 92 having a disk-like shape, a diameter of 0.25 inches and a height of 0.125 inches. In this embodiment, the inserter shaft 94 has a length of 1.5 inches and outside threads or other features at the distal end of the inserter shaft 94 to facilitate connection to the tip. In this specific embodiment, the momentum transfer members 98 can have a length of 0.375 inches and a diameter of 0.0626 inches.

Referring to FIG. 1, the head 110 of the insertion device 10 may provide the foundation 112 for the position bias member, may close the distal end of the inserter chamber 82, and may help align and direct the inserter 90 during operation. The head 110 may be generally cylindrical at the proximal end of the head 110 and may be conical at the distal end of the head 110. The head 110 may be connected to the distal end of the housing 80 at a connection which can be interference fit, threaded, slot-lock, detents, or any other suitable connection mechanism. The head 110 may include a foundation 112 for the position bias member 100 that maintains the position bias member 100 between the inserter head 92 and the foundation 112. The head 110 may include a head aperture 114 that allows the inserter shaft 94 to extend beyond the distal, conical end of the head 110. A sufficient space or tolerance is allowed between the inner surface of the head aperture and the outer surface of the inserter shaft for movement of the shaft during insertion while also maintaining position accuracy (i.e. reducing looseness or play between the two members).

The tip 120 provides the interface between the inserter shaft 94 and the therapeutic device 16. The tip 120 may be connected to the distal end of the inserter shaft 94 by threads, interference fitting, gluing, welding, or other suitable mechanism. The tip 120 may define at least one tip aperture 122, which is in fluid communication with the inserter conduit 96. The tip 120 may be configured in a variety of shapes. In one embodiment, the tip 120 is conical at the proximal end of the tip 120 where it may connect with the inserter shaft 94 and substantially flat on the distal surface of the tip 120. The tip 120 may also include multiple tip apertures to facilitate retention and insertion of a therapeutic device having varied shapes or non-planar contours. The tip 120 may also be coated with a flexible substance, such as silicone, to facilitate retention and insertion of a therapeutic device 16 and provide for increased interface contact between the tip and the therapeutic device sufficient to increase a vacuum seal between these surfaces.

In order to retain the therapeutic device at the tip, a vacuum control system can be operatively connected to the device. As shown in FIG. 1, a first vacuum source 14 can be fluidly coupled to the inner chamber 42 at the first vacuum inlet 24. This first vacuum provides a vacuum to the inner chamber 42 behind or at a back side of the piston 70, at the proximal end of the outside barrel 40, moving the piston to the proximal end of the inner chamber. A second vacuum source 12 can be fluidly coupled to the axial chamber 52 via the second vacuum inlet 28. This second vacuum provides a vacuum to the axial chamber 52 behind the therapeutic device 16, at the proximal end of the outside barrel 40 through the momentum transfer members 98 and inserter axial conduits to the tip 120.

A pressure control system can be used to manipulate the two vacuum sources such that the movement of the piston and suction/release of the therapeutic device can be coordinated. The pressure control system is capable of independently controlling each of the vacuum pressures supplied by each of the first and second vacuums (12 and 14) described above. In one embodiment of the insertion device 10, movement of the piston can be substantially entirely controlled by sequential application of vacuum and then positive pressure and retention and release of the therapeutic device 16 can be substantially entirely controlled by the second vacuum 12.

This pressure control system is capable of generating an insertion speed for the therapeutic device 16 approximately from 8-12 meters per second. The pressure control system incorporates a timing circuit that delivers positive pressure behind the therapeutic device 16 after insertion, which helps ensure that the therapeutic device 16 is released from the tip 120. For example, a compression source can also be attached to the inlet 28 and pressure relief valves can be added to allow manipulation of a piston driving pressure and the amount of vacuum force at the tip. This allows for insertion pressure and vacuum pressures to be readily controlled and adjustable depending on the specific therapeutic device and/or conditions. Also, the second vacuum 12 may be utilized to retrieve a therapeutic device 16 after insertion. The valves can be controlled by a timing circuit. These valves can be three way so that they switch between a compression source and a vacuum source. The amount of applied pressure is controlled by a pressure relief valve on each line. Timing of each valve to the open or closed position can be changed, and the suction is controlled to release the therapeutic device. For example, suction can be released approximately 100 ms after the piston is fired. As a general guideline, the duration of the compression behind the piston can vary from 10-500 ms.

FIG. 11 illustrates another alternative embodiment of the insertion device 10 where the movement of the piston 70 is controlled by adjusting differential pressure on the back and front sides of the piston. The piston 70 can be slidably contained in an inner chamber 42. The piston 70 is allowed to move within the inner chamber from a proximal end to a distal end of the inner chamber 42. The piston 70 can include a momentum transfer member 98 that extends toward the distal end of the inner chamber 42. The distal end of the inner chamber 42 can also include a piston stop 60 configured to limit motion of the piston 70 and allow the momentum transfer member 98 to extend therethrough.

Figure 12:
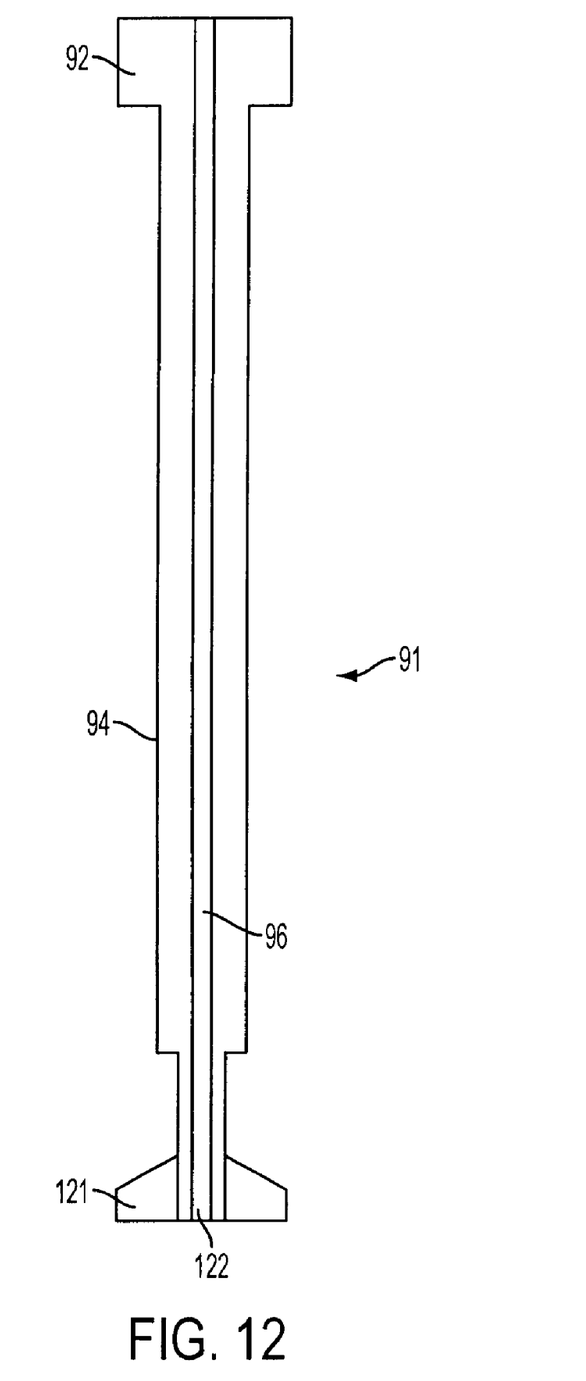
FIG. 12 is a side cross-sectional view showing dimensions of an alternative inserter tip having a flanged tip portion in accordance with another embodiment of the present invention.

A first vacuum 12 is attached to the inner chamber 42 at the proximal end of the inner chamber 42. This first vacuum 12 provides a first pressure to the inner chamber 42 behind the piston 70, or at a back side of the piston 70 proximate to the proximal end. A second vacuum 14 can be operatively associated with the distal end of the inner chamber 42 via an outer axial chamber 52. The axial chamber 52 may be in fluid communication with the inner chamber 42 and the inserter conduit 96, as illustrated in FIGS. 11 and 12. This second vacuum 14 provides a second pressure in front of the piston 70, or at a front side of the piston 70, opposite the back side of the piston 70.

A pressure control system is used to manipulate the two vacuum sources. The pressure control system is capable of independently controlling each of the vacuum pressures supplied by each of the first and second vacuums (12 and 14) described above. In this manner movement of the piston 70 can be substantially entirely controlled by varying the relative strength of each vacuum and optionally positive pressures applied to the back side of the piston via conduit 24.

An inserter can be slidably contained in a housing 80 proximate the distal end of the inner chamber 42 opposite the piston stop 60. This inserter includes an inserter conduit 96 extending along a transverse axis of the inserter and an inserter head 92. The inserter conduit allows fluid communication between the distal end of the inner chamber 42 and a tip 120 of the inserter.

A position bias member 100 can be operatively associated with the inserter and configured to bias the inserter toward the piston stop 60 in a biased position. The position bias member 100 can generally be a spring, although other mechanisms can also be used such as, but not limited to, flexible tabs, elastic restraints, and the like.

The housing 80 also may include a vent 84, or multiple vents 84, oriented to allow fluid communication with the distal end of the inner chamber 42 when the inserter is in an unbiased position. As shown in FIG. 11, the vents 84 can be oriented circumferentially around the housing 80 between the piston stop 60 and the tip 120. Typically, the vents 84 can be oriented within about 1-2 mm of the piston stop 60 in order to readily release the pressure generated by the second vacuum 14.

The momentum transfer member 98 of the insertion device 10 must generally extend beyond the piston stop 60. The portion which extends beyond the piston stop 60 can be adjusted in length in order to balance momentum and mechanical transfer mechanisms. This allows the inserter tip 120 to be moved by both mechanical and momentum transfer means. In one preferred embodiment, the momentum transfer member 98 can include a portion which extends up to and in contact with the inserter tip 120 but does not extend more than about 0.1 mm beyond the piston stop 60. In another embodiment, the momentum transfer member 98 can extend further past the piston stop 60. A longer momentum transfer member generally corresponds to a larger degree of mechanical movement, i.e. inelastic collision, of the inserter tip while a shorter transfer member corresponds to a larger degree of momentum transfer, i.e. elastic collision.

The inserter chamber 82 and/or inserter head 92 may be configured to allow insertion of a particular length of therapeutic device 16. In particular, an inserter chamber 82 may have a predetermined length that only allows the inserter head 92 to travel a predetermined distance to prevent the inserter tip 120 from traveling a farther distance than the length of corresponding electrodes on a therapeutic device 16 to be inserted. Several different interchangeable tips can be provided for varying insertion depths. Alternatively, an inserter chamber 82 may have a given length and the width of the inserter head 92 may be varied to increase or decrease the actual distance inside the inserter chamber 82 where the inserter head 92 moves transversely, thus the tip 120 is prevented from traveling a farther distance than the length of the corresponding electrodes on a therapeutic device 16 to be inserted. Similarly, mechanical stops can be provided within the inserter chamber 82 to adjust the insertion depths. For example, FIG. 12 shows an alternative inserter assembly 91 similar to that illustrated in FIG. 11 where the inserter chamber 82 defines the distance the inserter head 92 can move during operation and therefore also controls the insertion depth of a therapeutic device 16. Thus, a therapeutic device 16 having a desired 1.5 mm insertion depth can use an inserter chamber 82 that allows the inserter head 92 to travel 1.5 mm.

Referring again to FIG. 1, during operation, the first vacuum pressure of the insertion device 10 can be adjusted to move the piston 70 toward the proximal end of the inner chamber 42. In contrast, the first vacuum pressure can be released to allow movement of the piston 70 toward the distal end of the inner chamber 42. Valves controlling each of the first and/or second pressures can be a needle valve or any other mechanism which allows for fine control of pressure. The second pressure of the insertion device 10 can be reduced to pickup a therapeutic device 16. This is also how the inserter tip 120 can be used to retrieve a therapeutic device 16.

Although a wide range of insertion speeds can be achieved, this method of manipulating the two vacuum sources of the insertion device 10 can achieve a rate of insertion speed of approximately 8-12 meters per second. This relatively fast insertion speed appears to be an optimal range which allows for complete electrode insertion, reduced tissue damage, and minimizes potential for electrode damage.

In accordance with the present invention, the insertion device 10 can be configured for disassembly to allow easy replacement of parts, cleaning, sterilization, and adjustment. For example, referring to FIGS. 1 and 11 a threaded engagement (not shown) can be prepared near either end of the outside barrel 40 to allow removal or replacement of the piston 70. Similarly, a threaded engagement (not shown) can be provided for removal and/or replacement of the inserter 90 and/or inserter tip 120.

The insertion device 10 may also be formed by single parts that perform the same function as previously described multiple parts. For example, the outside barrel 40 and the housing 80 may be a single, continuous piece, which may also include the central tube 50 that creates the inner chamber 42 and the axial chamber 52. Also, the inserter shaft 94 and the tip 120 may be a single, continuous piece. Also, the piston stop 60 may be formed as part of the outside barrel 40 and/or housing 80. There are numerous combinations of pieces of the insertion device 10 that may be combined into a single piece, or separated further into individual pieces, while maintaining the function of the resulting insertion device 10. One reason for developing insertion devices 10 composed of fewer separate parts may be to facilitate development of a single-use insertion device that may be specially designed for a specific therapeutic device 16.

A variety of methods may be employed to help insert a therapeutic device 16 into different types of organic tissue. The tip 120 of the insertion device 10 can be formed to any functional shape. In one embodiment, tips 120 can have a conical shape. Alternatively, the tips 120 can form a flanged inverted cone which flares outward, as illustrated in FIG. 1. In this embodiment, the tip 120 can have a larger surface area over which to contact the therapeutic device 16 which can help to improve contact with a backside of the therapeutic device 16. Additionally, the tip 120 may contain more than one tip aperture 122. This is particularly beneficial when the therapeutic device 16 has an uneven or rough surface. In yet another alternative aspect of the invention, the tip 120 of the insertion device can be coated with a flexible material which improves sealing of the vacuum upon contact with a therapeutic device 16. One currently preferred flexible material can include or consist essentially of silicone.

Further, the insertion devices 10 of the present invention can include members which help to control penetration depth of the therapeutic device 16. The insertion device 10 shown in FIG. 11 will have an insertion depth which is at least partially determined by the distance that the insertion device 10 is held from the tissue during insertion. However, there is some margin of leeway as the tissue can flex upon insertion when impacted. This does not guarantee that the therapeutic device 16 will be fully inserted. Therefore, in one alternative embodiment, the tip 120 of the insertion device 10 can be fitted with a sleeve to control the depth of the insertion. The sleeve can extend past the tip 120 and encompass the therapeutic device 16, when present. The length of the sleeve can then be useful in adjusting insertion depth for different therapeutic device 16, i.e. therapeutic device having longer or shorter electrodes. The sleeve may be formed into a variety of shapes, such as curved.

The method for inserting a therapeutic device 16 utilizing the present insertion device 10 will now be described. The present insertion device 10 utilizes at least two vacuum sources and a dual vacuum/pressure control system. The dual vacuum/pressure control system can be manipulated to control motion of the piston 70. The piston 70 transfers momentum to an inserter 90 which can similarly be slidably disposed within the insertion device 10. Manipulation of the dual vacuum/pressure control system enables a rate of insertion of approximately 8-12 meters per second to be achieved.

The dual vacuum/pressure control system can be set in a predetermined condition for inserting the therapeutic device 16. For example, the first vacuum pressure can be smaller than the second vacuum pressure before insertion such that the piston 70 is held against a proximal end of the insertion device 10 from the tip 120 while a vacuum is being pulled through the tip 120 and/or inserter shaft 94. The therapeutic device 16 is loaded onto the tip 120 and/or inserter shaft 94 of the insertion device 10 and held in place via vacuum suction. The second vacuum pressure holds the therapeutic device 16 onto the inserter tip 120. The fact that a vacuum pressure holds the therapeutic device 16 onto the inserter tip 120 will be beneficial for wireless therapeutic device 16 because there will be no lead wires to manage during the insertion process and positioning the therapeutic device 16 can be accomplished by appropriate positioning of the insertion device 10.

The insertion device 10 is then placed adjacent to a surface of organic tissue that is intended to receive the therapeutic device 16. Adjacent refers to a distance which is sufficiently close so as to achieve the desired effect. Adjacent can generally refer to actual direct contact, although small distances can be allowable. For example, in some cases it may be acceptable to allow up to about 0.3 mm distance between the device and the organic tissue, depending on the insertion device 10 and/or inserter 90 configuration. Placement of the insertion device 10 can be achieved either by hand or by using a suitable mechanism, e.g. a stereotaxic device.

The insertion device 10 can then be triggered by adjusting the relative pressure of the two vacuums so as to insert the therapeutic device 16 into the organic tissue. In one embodiment, the first vacuum pressure is rapidly increased to move the piston 70 toward the distal end, or second end, of the inner chamber 42. The piston 70 impacts the piston stop 60, and in some embodiments the momentum transfer member 98, causing the inserter 90 to rapidly insert the therapeutic device 16 into the organic tissue. As the inserter tip 120 inserts the therapeutic device into the organic tissue, the second vacuum pressure is switched to a positive pressure to facilitate release of the therapeutic device 16 from the inserter tip. The dual vacuum pressure control system utilizes a timing chip to switch the second vacuum pressure to a positive pressure at the appropriate moment.

In one embodiment, the first vacuum pressure becomes larger than both the second vacuum pressure and atmospheric pressure. As the first vacuum pressure becomes larger than both the second vacuum pressure and atmospheric pressure, the piston 70 moves toward the distal end, or second end, of the inner chamber 42. The piston 70 impacts the piston stop 60, and in some embodiments the momentum transfer member 98, causing the inserter 90 to rapidly insert the therapeutic device 16 into the organic tissue. As the inserter tip 120 moves toward the organic tissue, a series of vents 84 are opened to the atmosphere. This reestablishes atmospheric pressure on the back of the inserter tip 120 and releases the vacuum pressure holding the therapeutic device 16, thus allowing the therapeutic device 16 to be released from the inserter tip. The first vacuum pressure can then be returned to its original value causing the piston 70 to return to the proximal end of the inner chamber 42. The position bias member 100 in the housing 80 pushes the inserter 90 back toward the piston stop 60, blocking the vents 84 and restoring the second vacuum pressure. This change in relative pressures can be timed in order to prevent bouncing of the piston 70 against the piston stop 60 multiple times. Rather, it is generally desirable to adjust the pressures such that the piston 70 impacts the piston stop 60 a single time for each insertion. The use of relative pressure control across two ends of the piston 70 allows for elegant control of the piston 70 movement.

With respect to the embodiment illustrated in FIG. 11, the dual pressure insertion device 10 results in less recoil during insertion as compared to previous insertion devices utilizing more mechanical means of insertion. Likewise, this insertion device 10 minimizes debris from the insertion device, which can occur during insertion of a therapeutic device 16 by allowing debris to be removed via vacuum source 14 through inlet 28.

The preferable pressure for the second vacuum pressure depends on the size of the therapeutic device 16 to be inserted. Likewise when retrieving a therapeutic device 16, the preferable pressure for the second vacuum pressure depends on the size of the therapeutic device 16 to be retrieved.

As an example and not be way of limitation, a suitable pressure for the second vacuum pressure to insert a 4×4 UEA therapeutic device 16 can be from approximately 4 in Hg to about 4.5 in Hg below atmospheric pressure. Lower pressures result in the first vacuum pressure becoming larger than the second vacuum pressure, causing the piston 70 to rest at the distal end of the inner chamber 42 as opposed to the proximal end of the inner chamber 42. Higher pressures result in the strongest possible suction force not being applied, which then limits the range the insertion device 10 can be moved without dropping the therapeutic device 16.

The second vacuum pressure can be between 4-4.5 in Hg below atmospheric pressure to better attach a therapeutic device 16 if the resting value for the first vacuum pressure is also decreased. One parameter that largely determines the minimum value for the second vacuum pressure is that the second vacuum pressure can be greater than the first vacuum pressure and less than atmospheric pressure.

The dual vacuum pressure control system may also be manipulated in a manner that allows retrieval of the therapeutic device 16. Generally, the relative vacuum pressures can be reversed from the insertion process in order to retrieve or pick up a therapeutic device 16. As an example and not by way of limitation, the preferable pressure for the second vacuum pressure to retrieve a 4×4 UEA therapeutic device 16 can be approximately 6 in Hg below atmospheric pressure, or less. The preferable pressure for the second vacuum pressure to retrieve a 10×10 UEA therapeutic device 16 can be approximately 8 in Hg below atmospheric pressure, or less.

FIG. 12 illustrates an alternative inserter assembly 91 having a flanged or expanded tip 121 which increases contact area with a UEA or other similar substantially planar therapeutic device 16. This flanged inserter 91 is interchangeable with the inserter 92 shown in FIG. 11.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive.

What is claimed and desired to be secured by Letters Patent is:

1. A therapeutic device insertion device, comprising:
a piston slidably contained in an inner chamber to allow movement of the piston from a first end to a second end of the inner chamber, said second end including a piston stop configured to limit motion of the piston, said piston including a momentum transfer member extending toward the second end and able to extend through said piston stop;
a first vacuum operatively associated with the inner chamber at the first end providing a first pressure to the inner chamber at a back side of the piston proximate to the first end;
a second vacuum operatively associated with a first end of an axial chamber and providing a second pressure within the axial chamber, said second vacuum being operatively associated with the first end of the axial chamber and the second end of the inner chamber and providing the second pressure at a front side of the piston opposite the back side;
a pressure control system capable of independently controlling vacuum pressures supplied by each of the first and second vacuums;
an inserter slidably contained in a housing proximate the second end opposite the piston stop, said inserter including at least one aperture extending along a transverse axis of the inserter to allow fluid communication between the axial chamber and a tip of the inserter and the second pressure sufficient to retain a therapeutic device at the tip, said inserter including at least one aperture extending along the transverse axis of the inserter which also allows fluid communication between the second end of the inner chamber, the axial chamber and a tip of the inserter, and said housing including at least one vent oriented to allow fluid communication with the second end of the inner chamber when the inserter is in an unbiased position; and a position bias member operatively associated with the inserter and configured to bias the inserter toward the piston stop in a biased position.

2. The insertion device as in claim 1 said inner chamber is concentrically oriented around at least a portion of the axial chamber, said axial chamber and said inner chamber being fluidly independent from one another.

3. The insertion device as in claim 1 wherein said inserter includes at least one momentum transfer member extending through the piston stop so as to move said inserter by both mechanical and momentum transfer means.

4. The insertion device as in claim 1 wherein said second pressure is reducible to pick up the therapeutic device.

5. The insertion device as in claim 1 wherein a rate of insertion speed of approximately 8-12 m/s is achieved.

6. The insertion device as in claim 1 wherein said tip is fitted with a sleeve to control the depth of the insertion.

7. The insertion device as in claim 6 wherein said sleeve is curved.

8. The insertion device as in claim 1 wherein said tip forms a cone.

9. The insertion device as in claim 1 wherein said tip is coated with silicone.

10. The insertion device as in claim 1 wherein said first pressure is solenoid valved open to move said piston toward said second end and said first pressure is solenoid valved closed to move said piston toward said first end.

11. The insertion device as in claim 1 wherein said second pressure is reducible to pickup a therapeutic device.

12. A method for inserting a therapeutic device comprising:

providing an insertion device that utilizes at least two vacuums to control retention of the therapeutic device at a tip of the inserter and to control motion of a slidable piston which transfers momentum to an inserter sufficient to insert the therapeutic device at a rate of insertion of approximately 8-12 meters per second, and wherein the insertion device utilizes a dual vacuum pressure control system to control motion of the slidable piston by applying a separate relative pressure to opposite sides of the piston;

setting the dual vacuum pressure control system in a predetermined condition for inserting the therapeutic device;

loading the therapeutic apparatus onto the tip of the inserter of the insertion device;

placing the insertion device adjacent and substantially normal to a surface of organic tissue to receive the therapeutic device; and triggering the insertion device sufficient to at least partially embed the therapeutic device into the organic tissue, wherein triggering occurs by adjusting relative pressure of the two vacuums so as to insert the therapeutic device into the organic tissue.

13. The method of claim 12 wherein a first vacuum of the at least two vacuums is used to retain the therapeutic device at the tip and a second of the at least two vacuums is used to control motion of the slidable piston, wherein each of the first and second vacuums are fluidly independent from the other.

14. The method of claim 13 wherein the first vacuum occurs in an axial chamber oriented along a central axis of the insertion device and the second vacuum occurs in a concentrically oriented inner chamber having the slidable piston therein.

15. The method of claim 12 further comprising removing the therapeutic device from the organic tissue using a vacuum at the tip of the inserter.

16. The method of claim 12 wherein the tip of the inserter has a silicone coating to act as a seal for increased traction with a therapeutic device having a non-planar or imperfectly planar back.

17. The method of claim 12 wherein the step of triggering includes transferring momentum from the slidable piston to the inserter via a momentum transfer member which extends through a piston stop and contacts the inserter, said piston stop being oriented to separate the slidable piston from the inserter.

18. The method of claim 17 wherein the momentum transfer member is biased against the piston stop using a spring.

* * * * *

UNITED STATES PATENT AND TRADEMARK OFFICE
CERTIFICATE OF CORRECTION

| | | |
|---|---|---|
| PATENT NO. | : 8,226,661 B2 | Page 1 of 1 |
| APPLICATION NO. | : 12/055053 | |
| DATED | : July 24, 2012 | |
| INVENTOR(S) | : Kyle Balling et al. | |

It is certified that error appears in the above-identified patent and that said Letters Patent is hereby corrected as shown below:

In the Specification

Column 1, line 12, add:

GOVERNMENT INTEREST

This invention was made with government support under NS039677 awarded by the National Institutes of Health. The government has certain rights in the invention.

Signed and Sealed this
Twenty-third Day of June, 2015

Michelle K. Lee
*Director of the United States Patent and Trademark Office*